United States Patent [19]

Engler et al.

[11] 4,438,202

[45] Mar. 20, 1984

[54] STABLE, BASE SERUM COMPOSITIONS AND PREPARATION THEREOF

[75] Inventors: Philip V. Engler, Tarrytown; Steven N. Buhl, Nyack, both of N.Y.

[73] Assignee: Technicon Instruments Corporation, Tarrytown, N.Y.

[21] Appl. No.: 325,791

[22] Filed: Nov. 30, 1981

[51] Int. Cl.³ .................. G01N 33/16; G01N 33/48; C09K 3/00
[52] U.S. Cl. .................................. 436/8; 436/16; 436/175; 436/176; 436/825
[58] Field of Search .................. 23/230 B; 436/8–16, 436/17, 174–177, 825; 252/408.1

[56] References Cited

U.S. PATENT DOCUMENTS

| | | | |
|---|---|---|---|
| 3,955,925 | 5/1976 | Proksch et al. | 23/230 B |
| 4,045,176 | 8/1977 | Proksch et al. | 23/230 B |
| 4,158,544 | 6/1979 | Louderback | 23/230 B |
| 4,264,471 | 4/1981 | Briggs | 252/408 |

OTHER PUBLICATIONS

Mitra, G. and Lundblad, J., Biotechnology and Bioengineering, vol. 20, No. 7, pp. 1037–1044 (1978).

*Primary Examiner*—Benjamin R. Padgett
*Assistant Examiner*—M. Moskowitz
*Attorney, Agent, or Firm*—Morgan, Finnegan, Pine, Foley & Lee

[57] ABSTRACT

A consistent, stable serum having good optical qualities and improved filterability suitable for control and calibration uses is disclosed as well as its method of preparation.

31 Claims, No Drawings

STABLE, BASE SERUM COMPOSITIONS AND PREPARATION THEREOF

BACKGROUND OF THE INVENTION

This invention relates generally to the preparation of a very consistent serum having clear optical properties without significant loss of macromolecular lipid components. The processed serum is characterized by improved filterability and thermodynamic properties, which properties make the serum well suited for extended storage either as a sterile liquid or in a frozen state. The processed serum also exhibits improved lyophilization and rehydration properties when used in making calibrators and controls.

To date, there is no known method or procedure predicated upon the extraction of acid precipitable molecules and/or fractions to provide a stable, uniquely filterable and optically clear serum well suited and highly practical for use in making calibrators and controls.

SUMMARY OF THE INVENTION

In accordance with this invention, there is claimed a method for preparing a stable, consistent serum having clear optical qualities and improved filterability which comprises the steps of insolubilizing a component or components of said serum, separating said insolubilized component or components from the serum, and stabilizing the separated serum.

In a preferred embodiment, the starting serum is bovine serum.

In another embodiment, the insolubilization step is effected by reducing the pH of the serum below about pH 5, preferably by the addition of an inorganic or organic acid.

In still another embodiment, the separation step is effected bu passing through a filtering material or by centrifugation.

In still another embodiment, the stabilization step or neutralization is effected by raising the pH of the separated serum to a pH in the range of about 7 to 8 by the addition of an inorganic or organic base.

This invention also contemplates the application of the aforesaid processed serum for control and calibration uses by combining the processed serum and conventionally added analytes.

This invention also includes within its purview a serum intermediate prepared by insolubilizing a component or components from a serum by rendering said serum more acidic and separating said component or components from the serum. The resulting serum intermediate may be stabilized as described above or may be lyophilized. The lyophilized material can be reconstituted and then stabilized.

DETAILED DESCRIPTION OF THE INVENTION

The novel processed sera of this invention, because of the highly desirable properties arising from such processing, are rendered well suited for extended storage. As a result of improved lyophilization and rehydration properties, they are especially useful for application as calibrators and controls.

In the past, serum to be employed for diagnostic purposes was not storable for any length of time, because turbid upon storage and was difficult to filter after standing for short periods. For example, unprocessed or untreated liquid bovine serum stored refrigerated began to deteriorate within 48 hours. Concurrent with this deterioration, the serum sample becomes turbid which adversely affects absorbance properties and is limited with respect to utility. Filtration becomes a difficult and time-consuming process and even upon effecting said filtration, the resulting serum suffers a clarity problem which becomes translated into an unsuitable feature for future application.

Accordingly, the distinct and real advantages of the processed serum obtained by the method of this invention are clearly evident. For instance, processed serum according to this invention can be stored in the frozen state at $-20°$ C. for longer than 8 months without deterioration or becoming turbid as compared to unprocessed bovine serum which deteriorates and becomes turbid within 6 months under similar conditions. Even more striking is the comparison at refrigerated liquid storage, i.e., at $2°-8°$ C. A processed bovine serum according to this invention will be storage stable under these conditions for up to about 2 weeks whereas an unprocessed sample deteriorates within 48 hours. This latter storage stability property is especially significant since it allows the technician to prepare and store relatively large quantities of serum formulation without risk of having to discard it because of deterioration. Obviously, it is also a time saving factor to be able to prepare larger quantities rather than small amounts in repeated fashion.

Accordingly, the method of this invention provides a stable, very consistent serum having clear optical properties without significant loss of macromolecular lipid components. The resulting processed serum exhibits physical properties which render it especially well suited to additional processing insofar as it has improved filterability and thermodynamic properties. These properties make the serum well suited for extended storage as a sterile liquid or in the frozen state. The processed serum also exhibits improved lyophilization and rehydration properties for use in making calibrators and controls.

In the method of this invention for preparing such processed serum, the raw serum, e.g. bovine serum, is subjected to an insolubilization step wherein preferably, the pH is reduced by the addition of an organic or inorganic acid. Preferably, the pH is adjusted below about 5, and more preferably to a pH range of 4 to 5 and more preferably to a pH range from 4.4 to 4.6.

Typically, for employment as a calibrator or control, bovine serum is treated according to the herein disclosed process, however, other nammalian sera can be processed by this method including equine and human serum. Additionally, plasma or defibrinated plasma can be used in this process.

The insolubilization step is generally effected by pH adjustment employing any organic or inorganic acid which does not interfere with the inherent nature of the serum or its prospective application. Typical acid examples are hydrochloric acid and acetic acid.

The cloudy serum after the insolubilization step is then treated by filtration or centrifugation to provide a clear liquid. The reason for the turbidity which results from pH lowering is not clearly understood. While not wishing to be held to any particular mechanism without further investigation, it is theorized that the acid precipitable molecules and/or fractions are protein or protein-related. In any event, the removal of this material appears to provide a serum that is inherently more stable and upon freezing has a better "crystal structure" and is essential in the herein disclosed method.

The removal thereof is accomplished by a separation step and can be effected by any suitable filtration procedure. For example, the adjusted pH serum can be filtered through a filter media of filter paper such as an asbestos-cellulose, cellulose or a fiberglass filter media. It has been found suitable to include a filter aid such as diatomaceous earth.

As an alternative, the separation can be suitably achieved by centrifugation.

After filtration, the serum is stabilized or neutralized, preferably by raising the pH of the separated serum to a pH of about 7 to 8, preferably 7.5 by the inclusion of any organic or inorganic base which does not interfere with the inherent nature of the serum or its prospective uses. Representative examples include soldium hydroxide and trihydroxyaminomethane.

The resulting processed serum has excellent storage properties, as discussed above, for it to be stored in substantial quantities for eventual use in or as calibration or control materials in diagnostic analyses.

Accordingly it can be formulated in the state obtained by the aforedescribed method even after substantial storage times or it can be lyophilized after the incorporation of conventionally employed analytes. The lyophilized material is extremely stable and can be easily reconstituted.

Typical analytes include glucose, potassium, alkaline phosphatase, creatine kinase, urea, lactate dehydrogenase (LDH), alanine-amino transferase, triglycerides, cholesterol, etc.

This invention also encompasses a serum intermediate obtained by insolubilizing a component or components of the serum by rendering the pH of said serum more acidic and separating said insolubilized component or components from said serum.

The resulting serum can be lyophilized or can thereafter be stabilized as described above. The lyophilized material can be reconstituted and then stabilized. In general, the analytes are not incorporated until the intermediate serum is stabilized.

EXAMPLE I

A pool of bovine serum (1000 l, pH 7.5) is adjusted to a pH of 4.4–4.6 with hydrochloric acid (3 M). At this pH, the serum becomes cloudy. A filter aid, e.g. diatomaceous earth (0.5% by weight) is added to this cloudy serum which is then passed through a filtration system, a filter housing containing CUNO 50S filter pads. The filtrate is adjusted to a pH of 7.5–7.7 with sodium hydroxide (4 M). The resulting processed serum exhibits the properties described herein.

Continuous flow centrifugation at 720,000 g with a 10 min. dwell time can be substituted for the filtration step.

EXAMPLE II

The processed serum of Example I is made into a calibrator or control by adding predetermined amounts of analytes glucose, potassium, alkaline phosphatase, creatine kinase, urea, lactate dehydrogenase (LDH), alanine-amino transferase (SGPT), triglycerides, cholesterol and other analytes used to calibrate any assay method or monitor control of any assay especially those of clinical importance. A more specific example of a control material is described in the Table which follows:

TABLE

| ANALYTE | NORMAL VALUE* |
|---|---|
| Albumin | 3.9 g/dl |
| Alk. Phos. | 100 U/L |
| Calcium | 7.0 mg/dl |
| CPK | 200 U/L |
| Chloride | 95 meq/L |
| Cholesterol | 220 mg/dl |
| $CO_2$ | 32 meq/L |
| Creatinine | 1.5 mg/dl |
| Glucose | 60 mg/dl |
| Inorganic Phosphorus | 2.5 mg/dl |
| LDH | 225 U/L |
| Potassium | 3.5 meq/L |
| Sodium | 140 meq/L |
| Total Bilirubin | 1.0 mg/dl |
| Total Protein | 7.0 g/dl |
| SGOT (aspartate amino-transferase) | 40 U/L |
| SGPT | 40 U/L |
| BUN (blood urea nitrogen) | 20 mg/dl |
| Triglycerides | 120 mg/dl |
| Uric Acid | 4.0 mg/dl |
| Total Iron | 150 ug/dl |
| GGT (gamma glutamyl transferase) | 40 U/L |
| Direct Bili. (bilirubin) | 0.1 mg/dl |

*Normal values as defined by assays on Technicon's SMAC, a registered Technicon trademark.

The formulated serum is then dispersed into aliquots, lyophilized or preserved for storage before use.

Prior to addition of analytes, the sodium and chloride levels of the processed serum can be reduced by any convenient procedure such as dialysis or diafiltration and the serum concentrated.

The serum can also be concentrated and the sodium and chloride levels reduced before pH treatment and filtration or centrifugation.

EXAMPLE III

The procedure of Example I is repeated wherein the serum after filtration is lyophilized. This lyophilized material can be reconstituted and stabilized as described in Example I.

EXAMPLE IV

The procedure of Example I is essentially repeated except that human serum is treated in lieu of bovine serum.

It should be understood by those skilled in the art that various modifications may be made in the present invention without departing from the spirit and scope thereof as described in the specification and defined in the appended claims.

What is claimed is:

1. A method for preparing a stable, consistent serum having clear optical qualities and improved filterability without significant loss of macromolecular lipid components which comprises the steps of insolubilizing a component or components of said serum by reducing the pH of said serum by an acid addition treatment, separating said insolubilized component or components from the serum and stabilizing the separated serum by raising the pH of said separated serum.

2. The method of claim 1 for preparing a consistent bovine serum wherein the serum is selected from bovine serum or plasma.

3. The method of claim 1 wherein said pH reduction results in a serum pH below about 5.

4. The method of claim 3 wherein said pH is from pH 4.4 to pH 4.6.

5. The method of claim 1 wherein said pH reduction step is effected by the addition of an acid selected from organic and inorganic acids.

6. The method of claim 5 wherein said acid is hydrochloric acid.

7. The method of claim 5 wherein said acid is acetic acid.

8. The method of claim 1 wherein said separation step is effected by filtration through filter media.

9. The method of claim 8 wherein a filter aid such as diatomaceous earth is employed with said filter media.

10. The method of claim 1 wherein said separation step is effected by centrifugation.

11. The method of claim 1 wherein said stabilizing step is effected by raising the pH of the separated serum to a pH in the range of about 7-8.

12. The method of claim 11 wherein said pH raising step results in a serum pH of about 7.5.

13. The method of claim 11 wherein said pH raising step is effected by the addition of a base selected from organic and inorganic bases.

14. The method of claim 13 wherein said base is sodium hydroxide.

15. The method of claim 13 wherein said base is trihydroxyaminomethane.

16. The method of claim 1 wherein said serum is selected from human serum or plasma.

17. The method of claim 1 wherein the resulting serum is frozen or lyophilized.

18. The product obtained by the method of claim 1.

19. The product obtained by the method of claim 17.

20. A method for preparing a serum intermediate without significant loss of macromolecular lipid components which comprises the steps of insolubilizing a component or components of said seruum by rendering the pH of said serum more acidic by an acid addition treatment, and separating said insolubilized component or components from said serum.

21. The method of claim 20 wherein the resulting serum is frozen or lyophilized.

22. The method of claim 20 wherein the resulting separated serum is stabilized.

23. The method of claim 22 wherein said stabilized serum is lyophilized.

24. The product obtained by the method of claim 20.

25. The product obtained by the method of claim 21.

26. The product obtained by the method of claim 22.

27. The product obtained by the method of claim 23.

28. A method for preparing a serum formulation for control and/or calibration application which comprises combining the serum processed according to claim 1 and an analyte or analytes conventionally incorporated in such formulations.

29. A method for preparing a stable, rehydratable serum formulation for control and/or calibration application which comprises lyophilizing a composite containing the serum processed according to claim 1 and an analyte or analytes conventionally incorporated in such formulations.

30. The stable, rehydratable serum formulation obtained by the method of claim 29.

31. The serum formulation of claim 30 in reconstituted form.

* * * * *

UNITED STATES PATENT AND TRADEMARK OFFICE
CERTIFICATE OF CORRECTION

PATENT NO.  : 4,438,202
DATED       : March 20, 1984
INVENTOR(S) : Phillip V. Engler and Steven N. Buhl It is certified that error appears in the above-identified patent and that said Letters Patent is hereby corrected as shown below:

Section [75] Inventors, change "Philip V. Engler" to

-- Phillip V. Engler --

Claim 20, column 6, line 4, change "seruum" to

-- serum --

Signed and Sealed this

Sixteenth Day of October 1984

[SEAL]

Attest:

Attesting Officer

GERALD J. MOSSINGHOFF

Commissioner of Patents and Trademarks